(12) United States Patent
Schwägli et al.

(10) Patent No.: US 12,109,001 B2
(45) Date of Patent: Oct. 8, 2024

(54) STERILE COVERING FOR AN OPTICAL DEVICE

(71) Applicant: Naviswiss AG, Brugg (CH)

(72) Inventors: Tobias Schwägli, Solothurn (CH); Charles Findeisen, Wettingen (CH); Thomas Hauri, Gränichen (CH)

(73) Assignee: Naviswiss AG, Brugg (CH)

( * ) Notice: Subject to any disclaimer, the term of this patent is extended or adjusted under 35 U.S.C. 154(b) by 1481 days.

(21) Appl. No.: 16/345,234

(22) PCT Filed: Oct. 20, 2017

(86) PCT No.: PCT/EP2017/076805
§ 371 (c)(1),
(2) Date: Apr. 25, 2019

(87) PCT Pub. No.: WO2018/077731
PCT Pub. Date: May 3, 2018

(65) Prior Publication Data
US 2019/0290378 A1    Sep. 26, 2019

(30) Foreign Application Priority Data

Oct. 28, 2016 (CH) ..................... 1455/16

(51) Int. Cl.
| A61B 46/10 | (2016.01) |
| A61B 34/10 | (2016.01) |
| A61B 46/00 | (2016.01) |
| G02B 27/00 | (2006.01) |
| A61B 34/20 | (2016.01) |
| A61B 90/00 | (2016.01) |

(52) U.S. Cl.
CPC .............. *A61B 46/10* (2016.02); *A61B 34/10* (2016.02); *A61B 46/40* (2016.02); *G02B 27/0006* (2013.01); *A61B 2034/2057* (2016.02); *A61B 2090/373* (2016.02); *A61B 2090/3937* (2016.02); *A61B 2560/0431* (2013.01)

(58) Field of Classification Search
CPC ... A61B 46/10; A61B 41/40; A61B 2090/373; A61B 2560/0431; F02B 27/0006
USPC ........................................................ 359/510
See application file for complete search history.

(56) References Cited

U.S. PATENT DOCUMENTS 3,698,791 A * 10/1972 Walchle .................. A61B 90/50
                                                             359/510
5,274,500 A * 12/1993 Dunn ...................... A61B 1/042
                                                             359/507
5,433,221 A *  7/1995 Adair ..................... A61B 46/10
                                                             128/853
(Continued)

FOREIGN PATENT DOCUMENTS

WO        2017079844 A1     5/2017

OTHER PUBLICATIONS

International Search Report received in PCT/EP17/76805, dated Jan. 23, 2018, pp. 6.
(Continued)

*Primary Examiner* — Ricky D Shafer
(74) *Attorney, Agent, or Firm* — Hard IP LLC (57) ABSTRACT

A sterile covering for an optical device comprises a window element and a shell. The shell is attached to the window element, the shell having an opening closed by the window element. A system comprises an optical device and a sterile covering.

13 Claims, 9 Drawing Sheets

(56) References Cited

U.S. PATENT DOCUMENTS

| | | | | |
|---|---|---|---|---|
| 5,682,264 | A * | 10/1997 | Cleveland | G02B 21/24 359/511 |
| 5,812,188 | A | 9/1998 | Adair | |
| 6,024,454 | A * | 2/2000 | Horan | G02B 21/0012 359/511 |
| 6,318,864 | B1 * | 11/2001 | Fukaya | A61B 46/10 359/368 |
| 6,459,538 | B2 * | 10/2002 | Grafenhain | G02B 21/24 359/513 |
| 8,146,825 | B1 | 4/2012 | Prpa | |
| 9,168,103 | B2 | 10/2015 | Hladio et al. | |
| 2001/0056221 | A1 * | 12/2001 | Verschuur | A61B 46/10 600/122 |
| 2002/0000231 | A1 | 1/2002 | McNeirney et al. | |
| 2002/0185136 | A1 * | 12/2002 | Faries | H01H 13/785 128/849 |
| 2005/0088763 | A1 * | 4/2005 | Weaver | G02B 21/0012 359/818 |
| 2005/0286130 | A1 * | 12/2005 | Bala | G02B 27/0006 359/507 |
| 2010/0076306 | A1 | 3/2010 | Daigneault et al. | |
| 2014/0261456 | A1 | 9/2014 | Malackowski et al. | |
| 2015/0366618 | A1 * | 12/2015 | Higuchi | A61B 90/50 359/510 |
| 2016/0374775 | A1 * | 12/2016 | Prpa | A61B 50/20 705/3 |
| 2017/0168292 | A1 * | 6/2017 | Koenig | G02B 21/02 |
| 2017/0333136 | A1 * | 11/2017 | Hladio | A61B 46/10 |

OTHER PUBLICATIONS

Written Opinion of the International Searching Authority received in PCT/EP17/76805, dated Jan. 23, 2018, pp. 6.

* cited by examiner

STERILE COVERING FOR AN OPTICAL DEVICE

CROSS-REFERENCE TO RELATED APPLICATIONS

This application is a U.S. national stage filing under 35 U.S.C. 371 of international patent application no. PCT/EP2017/076805, filed on Oct. 20, 2017, which claims priority to Swiss patent application no. CH01455/16, filed on Oct. 28, 2016, the contents of both of which are incorporated herein by reference in their entirety.

TECHNICAL FIELD

The invention relates to a sterile covering for an optical device. The invention relates to a system comprising a sterile covering and an optical device which can be covered by this sterile covering, for example, a handheld optical measuring system which can be used in particular in computer-assisted surgery.

Handheld optical measuring systems used in computer-assisted surgery have the advantage that they are held freehand in front of the measurement volume for measurements of, for example, measuring markers. For work steps for which no measurements are necessary, the measuring system is put aside. For work steps for which measurements are necessary, the measuring system is picked up again and held in front of the measurement volume.

The optical measuring systems must be sterile for their use in the immediate operating environment. According to a common practice optical devices or instruments, including any cables, are packaged in sterile, transparent pouches (hereafter the English term "drape" is commonly used in the art), which ensures a reliable barrier between the non-sterile optical measurement system and the sterile OR environment. Some optical measuring systems additionally require a window for the illumination of the measuring field or for imaging systems. An optical window is inserted into an opening of the drape. The window and the drape are interconnected to provide a reliable barrier between the non-sterile optical device or instrument and the sterile surgical environment.

The requirements for a sterile covering comprising a window element and a cover, which is particularly suitable for hand-held optical measuring systems, are manifold. In the following, this will be discussed using the example of a hand-held optical camera system for the measurement of measurement markers. Thus, the window element must be stable and can be fixed in a defined manner on the camera body, so that, for example, the previously determined parameters for the camera calibration remain valid. The cover must be sterilizable using common methods such as gamma irradiation.

When using an active illumination system integrated with the camera system, an undefined or stably mounted window element can promote unwanted direct optical crosstalk from the illumination to the imaging system. In particular, it is important that the window element does not come off the fixture even when abutting (deliberately or unintentionally) the camera system on objects. Also, it is advantageous that the sterile covering can be easily and quickly removed from the camera system after use. Usually, sterile covers are used once ("single-use"). Therefore, it is desirable to use sterile coverings manufactured at a low-cost.

DESCRIPTION OF RELATED ART

The prior art for drape systems for handheld optical devices is exemplified in U.S. Pat. No. 8,146,825 B2 (Prpa). A spring cap equipped with a window cap is placed on the optical device (in this case it is a barcode reader) with little pressure. The removal of the window is reversed by simply pulling on the cap. The drape is attached to the side of the window cap. The operation of the optical device, such as a handheld scanner, is also possible with the installed drape system. However, the Prpa patent does not elaborate on how the window is secured upon mechanical impact and whether the measuring capability of the optical device is ensured in each case.

The prior art for drape systems for optical, non-handheld (i.e., stationary) systems is described in numerous patents and patent applications, such as in the already mentioned U.S. Pat. No. 8,146,825 B2 (Prpa), in US 2014/0261456 A1 (Stryker Corporation) or in US 20100076306A1 (Daigneault). Also, in these patents is not discussed in more detail how the window element is secured during mechanical abutment to ensure the measurement capability of the measuring system. In the U.S. Pat. No. 9,168,103 B2 (Intellijoint Surgical Inc.) the window element is attached to the camera system using an additional clip.

In the described prior art, the secure attachment of the sterile covering to the measuring system is ensured mainly by the sterile covering itself, such as by directly integrated in the window element snap mechanisms or additional tools such as brackets, screw caps or elastic bands, which increases the costs for the manufacture of the sterile covering. Since a sterile covering is designed as a disposable article, the operating costs increase considerably due to the expensive covering.

SUMMARY OF THE INVENTION

The object of the present invention is to develop further a system for an optical device for computer-assisted surgery, which is in particular secured against slipping. In particular, the sterile covering of the system should be easy and quick to assemble and replace. In particular, the production of the sterile covering should be simple and inexpensive, so that the overall cost of the system can be reduced for the user.

The object is solved by the features of the claims. Advantageous developments are subject of the dependent claims.

When the term "for example" is used in the following description, this term refers to embodiments and/or variants, which is not necessarily to be understood as a more preferred application of the teachings of the invention. Similarly, the terms "preferably," "preferred," are understood to refer to an example of a set of embodiments and/or variants, which is not necessarily to be understood as a preferred application of the teachings of the invention. Accordingly, the terms "for example," "preferably," or "preferred," may refer to a plurality of embodiments and/or variants.

The following detailed description includes various embodiments of the inventive covering. The description of a particular covering is to be considered as exemplary only. In the specification and claims, the terms "including," "comprising," "having" are interpreted as "including, but not limited to."

A sterile covering for an optical device comprises a window element and a shell. The shell is attached to the window element, the shell having an opening which is closed by the window element. A sterile covering can include a sterilizable covering. A covering can be sterilized by a sterilization procedure so that a sterile covering can be obtained.

The shell can have an edge region, wherein the edge region is mounted on the window element. This edge region can have an edge that limits the opening according to this embodiment. The opening is thus surrounded by the edge region according to this embodiment. As a result, the shell can be easily connected to the window element, since the edge region forms a defined boundary, the edge, which is suitable for automated assembly. The edge can be produced in particular in a stamping process. For example, the shell and the window element can be connected by an adhesive or a welded connection. In particular, the window element has a sterile side, wherein the shell is mounted on the sterile side.

According to an embodiment, the edge region is arranged at least partially not directly adjacent to the edges of the window element. Thereby it is possible that the fastening adapter or the locking element mounted on the optical device can disappear under the shell. Optionally, a plurality of locking elements may be provided. In particular, a locking element and a fastening adapter can be provided. Optionally, a plurality of locking elements or a plurality of fastening adapters may be provided. The shell can be designed in particular as a flexible shell. Therefore, the dimensions of the fastening adapters and/or locking elements can be chosen arbitrarily, which makes it possible to use a sterile covering for a plurality of different fastening adapters or locking elements.

According to an embodiment, the window element includes a first layer and a second layer. By using a second layer, the dimensional stability of the window element can be increased. At least one of the first or second layers may form a reinforcing layer. At least one of the first or second layers may have a hole, so that measurement signals are not affected by optical effects, such as different refractive indices or reflection phenomena. In an embodiment, the first and second layers may be joined together by an adhesive bond. According to an embodiment, the window element may be printed on at least one side. In particular, the window element may contain one or more printed areas. Such a printed area can be an orientation aid for receiving the window element in a fastening adapter or in a locking element. In particular, a printed area can also absorb scattered light from a light source, so as not to falsify an optical measurement.

The invention also includes a system comprising an optical device and a sterile covering according to one of the preceding embodiments. In particular, the window element can be arranged above a measuring element of the optical device. According to an embodiment, the optical device comprises a fastening adapter or a locking element for the window element. Optionally, a plurality of locking elements may be provided. In particular, a locking element and a fastening adapter can be provided. Optionally, a plurality of locking elements or a plurality of fastening adapters may be provided. The locking element and the fastening adapter can be mounted on opposite side edges of the window element. The locking element can include a snap mechanism and/or an unlocking mechanism.

The system can be used for stationary or portable optical devices. In particular, the system can be designed as a stationary or a portable system.

The power supply or data transfer for the system can be provided by a cable. Alternatively, the power supply of the system can be autonomous, for example via accumulators, batteries. If the system includes a power cable, the sterile covering has an opening for the cable to pass through. The opening is preferably closable such that the outside of the sterile covering can be kept sterile, even if the inside of the sterile covering surrounds a non-sterile optical device. The inside of the sterile covering is located opposite to the optical device. A system with an autonomous power supply or autonomous data processing or data processing has the additional advantage that the optical device is completely closable by the sterile covering. According to this embodiment, the optical device is thus completely surrounded by the sterile covering. In particular, image data can be generated with the optical device, which can be processed locally.

In particular, it can be ensured using a system according to one of the preceding exemplary embodiments that all operating functions of the optical device can be carried out at the place of use without requiring a cable connection to a control unit. In particular, system-external functions, for example, the storage or printing of data, can be realized via a wireless connection. The optical device may, in particular, comprise a display device which is suitable for displaying results, for example in the form of text, images, videos.

An advantage of the sterile covering and the system according to the invention is that on the one hand the fastening adapter and the locking element for the window element are mounted directly on the optical measuring system and on the other hand, the sterile covering essentially consists of a combination of a window element and a shell, in particular, a drape attached to the window element, for example in the form of a bag or hose. The shells commonly used consist for example of polycarbonate or polyethylene.

A system according to one of the preceding embodiments can include a window element comprising an edge containing a chamfer or rounding.

According to an embodiment, the shell can cover the locking element or the fastening adapter.

BRIEF DESCRIPTION OF THE DRAWINGS

The drawings show embodiments of the sterile covering and the system comprising the optical device wrapped in the sterile covering. It is shown in.

DETAILED DESCRIPTION

Figure 1:
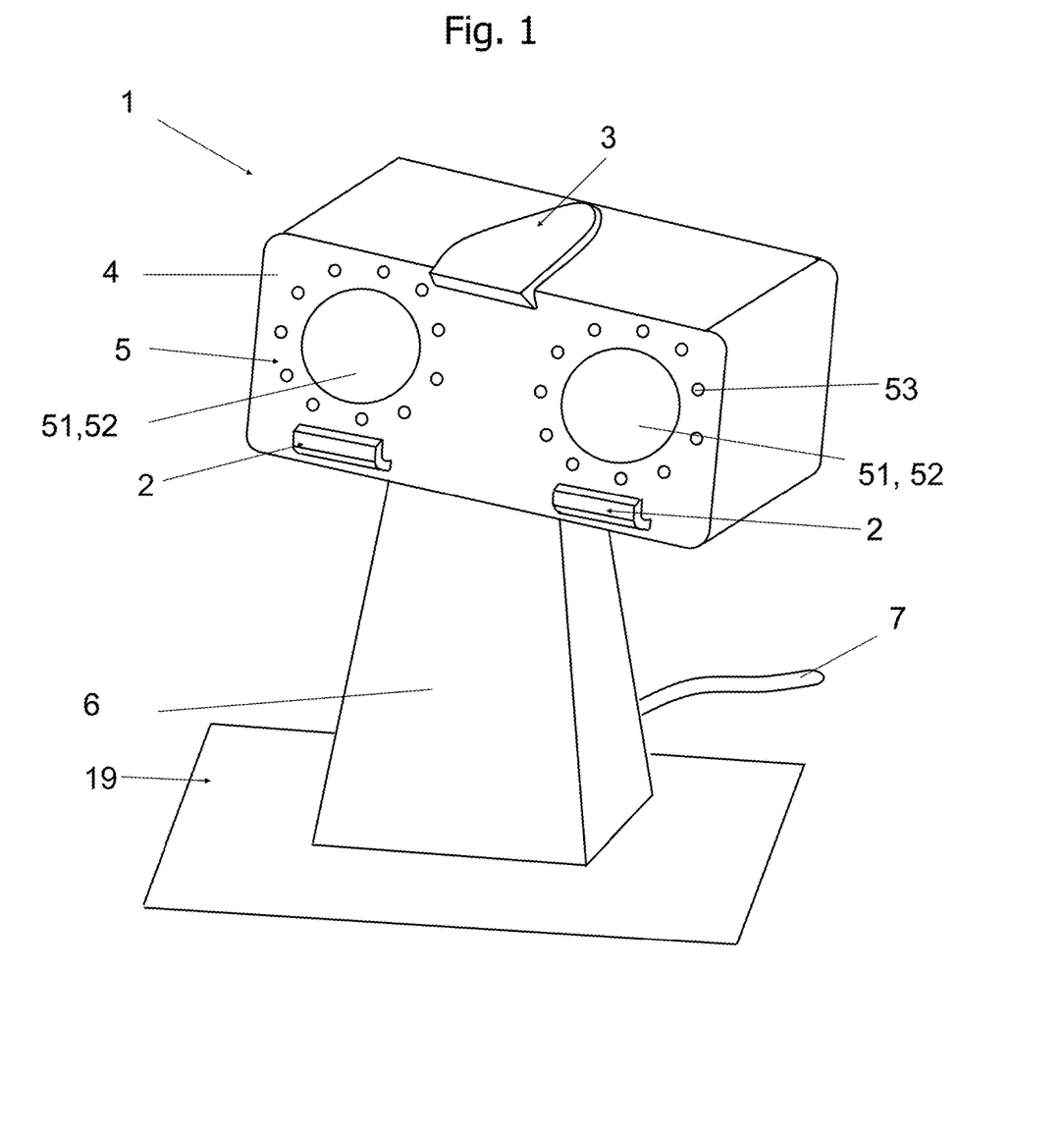
FIG. 1: a front side of an optical device according to a first embodiment.

FIG. 1 shows an overview sketch of an optical device 1 using the example of a stereo optical camera system comprising a fastening adapter 2 and a locking element 3 for a window element 12 of a sterile covering 10, the sterile covering 10 and the window element 12 being omitted in the present illustration. The sterile covering 10 and the window element 12 are shown for example in one of FIGS. 3 to 5. The optical side or front side 4 of the optical device 1 according to the present embodiment includes a window 5 associated with the optical device 1. The window 5 may consist of two circular openings for the two imaging systems, thus the objective 51 and the image sensor 52. The window 5 can include an LED ring assembly 53 for the active illumination of a measurement volume, not shown. According to the present embodiment, two fastening adapters 2 are provided. Instead of two fastening adapters 2, a single fastening adapter or more than two fastening adapters can be provided, which is not shown in the drawing. The use of two fastening adapters 2 has the advantage that the window element 12 of the sterile covering 10 is clearly defined in its position. The locking element 3 is used for temporary attachment of the window element 12 of the sterile covering 10 on the optical device 1.

The sketch is completed by a stand 6 on a table 19 and a cable 7 for energy and data transfer to the power supply, evaluation, and display module, not shown here. Alternatively, the cable 7 can be omitted. The power supply can be integrated with the optical device 1. The optical device 1 can communicate with external modules wirelessly. The stand 6 may also be formed as an adapter or contain an adapter to connect the optical device 1 fixed to a support or an object, which is not shown in the drawing. The outer surfaces of the optical device 1 are clean, but usually not sterile.

Figure 2:
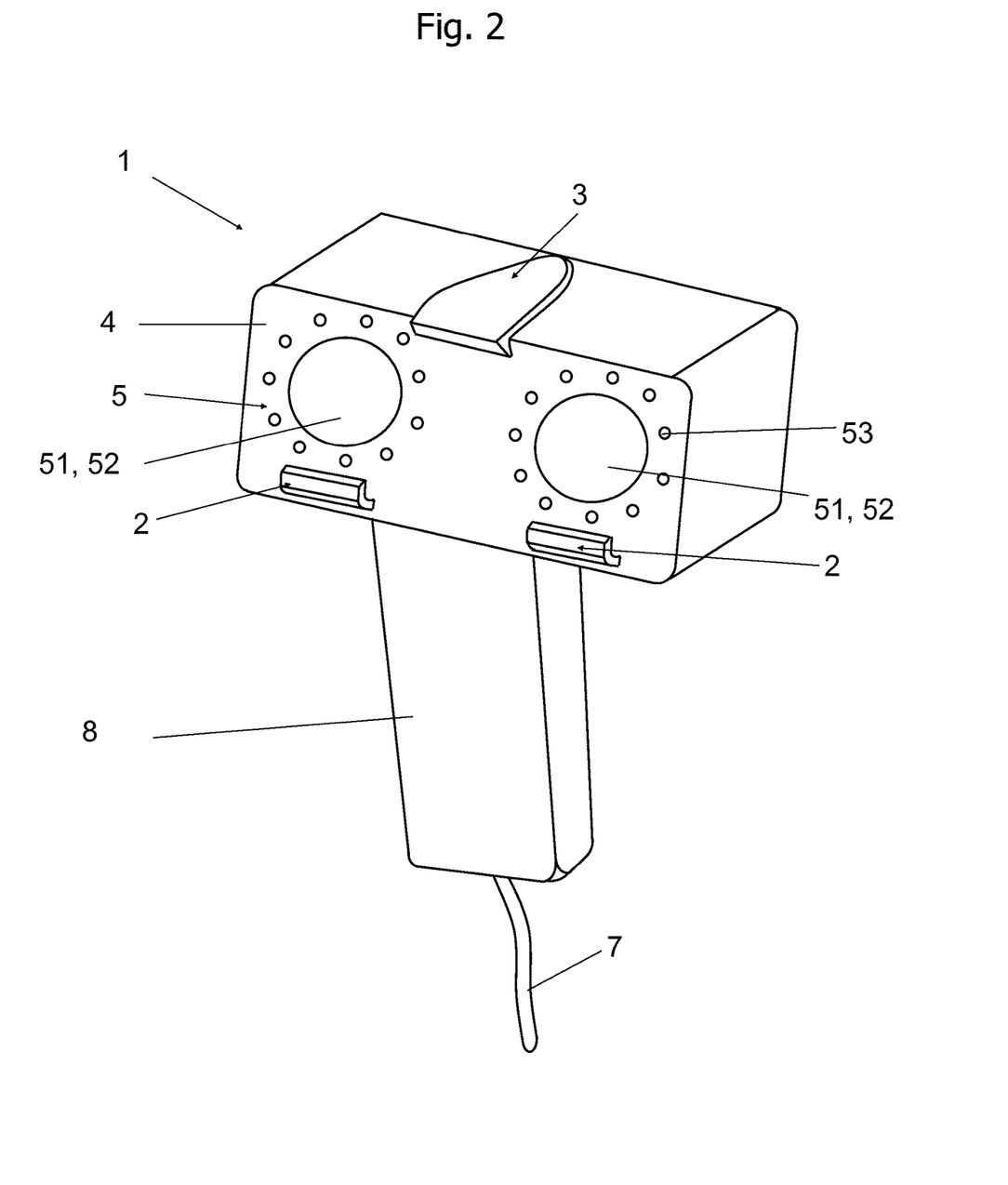
FIG. 2: a front side of an optical device according to a second embodiment.

FIG. 2 shows an overview sketch of an optical device 1 using the example of a handheld stereo optical camera system comprising a fastening adapter 2 and a locking element 3 for a window element 12 of a sterile covering 10. The sterile covering 10 and the window element 12 are omitted in FIG. 2. The optical side or front side 4 of the optical device 1 according to the present embodiment includes a window 5 associated with the optical device 1. The window 5 may consist of two circular openings for the two imaging systems, thus the objective 51 and the image sensor 52. The window 5 can include an LED ring assembly 53 for the active illumination of a measurement volume, not shown. The two fastening adapters 2 and the locking element 3 are used for the temporary fixation of the window element.

The sketch is completed by a handle 8 and a cable 7 for energy and data transfer to an energy supply and evaluation module, not shown here. Alternatively, the cable can be omitted. According to this variant, the power supply can be integrated with the optical device 1. The evaluation module can locally analyze data determined by the optical device. The optical device 1 can communicate with external modules wirelessly. The outer surfaces of the optical device 1 are clean, but usually not sterile. Handheld optical devices 1 used in computer-assisted surgery have the advantage that they are held freehand in front of the measurement volume for measurements of, for example, measuring markers (not shown here). For operations for which no measurements are necessary, the optical device 1 is put away. For work steps for which measurements are necessary, the optical device 1 is picked up again and held in front of the measurement volume.

Figure 3:
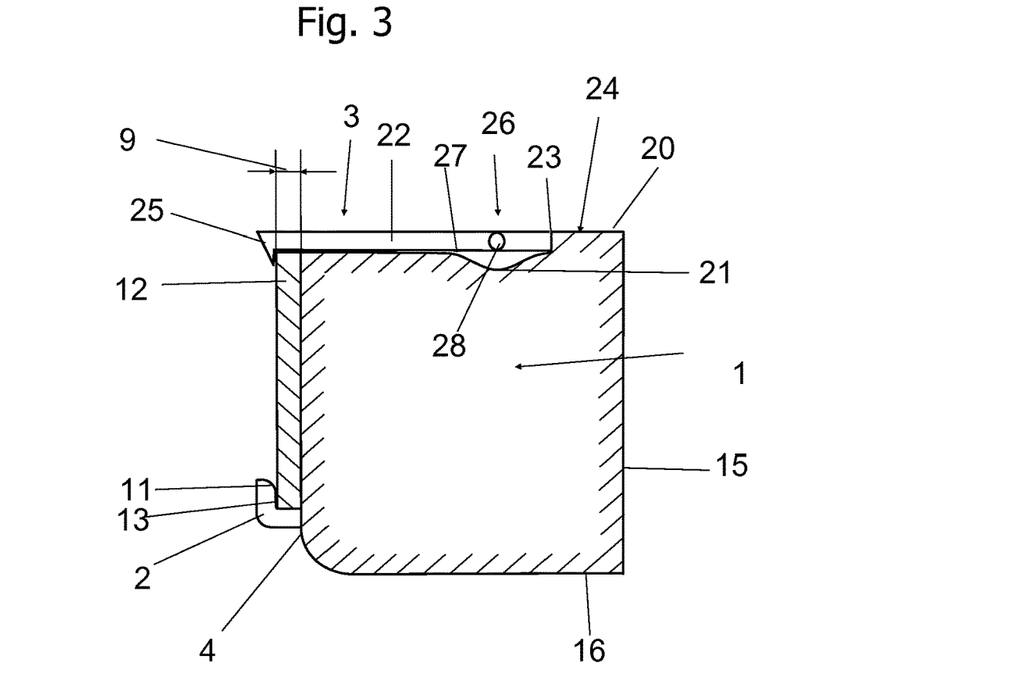
FIG. 3: a detail of the attachment of a window element of a system according to a first variant in the operating state.
Figure 5:
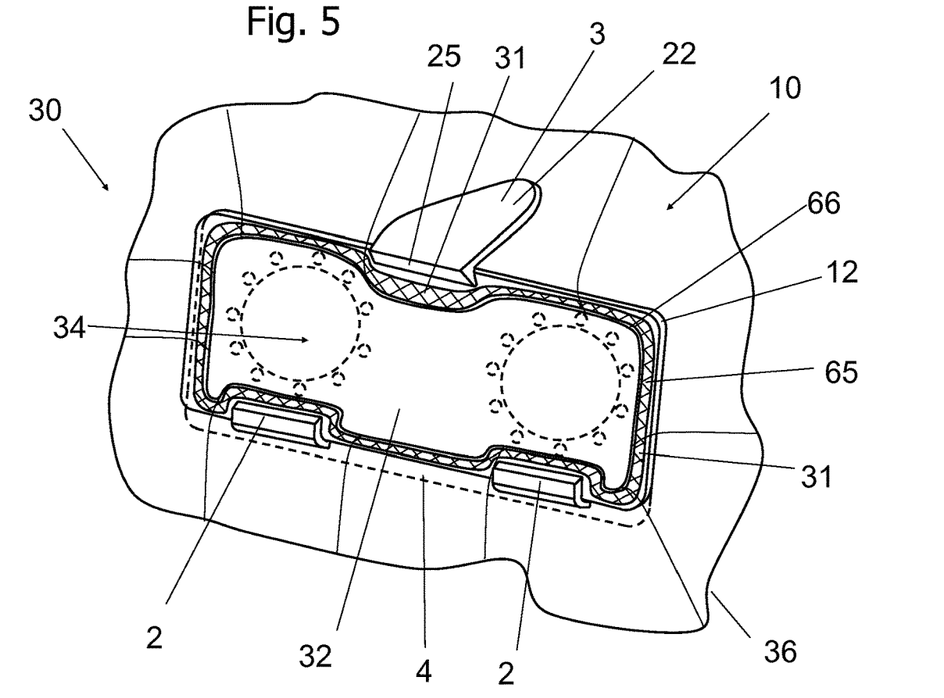
FIG. 5: the system according to the first variant according to one of the preceding embodiments.

FIG. 3 shows the attachment of a window element 12 of a sterile covering 10 of a system 30 according to FIG. 5 using a fastening adapter 2 and a locking element 3 on the front side 4 of the optical device 1 in a sectional view. The width of the gap between the front side 4 and the inner side of the fastening adapter 2 corresponds exactly to the thickness 9 of the window element 12. At least a part 11 of the inner side 13 of the fastening adapter 2 can be chamfered to facilitate the insertion of the window element 12. The term "chamfered" means that the inner side 13 can at least partially enclose an inclination angle relative to the plane of the window element 12 when installed.

The angle of inclination can be up to 15 degrees, preferably the angle of inclination is a maximum of 5 degrees. According to a variant, the inner side 13 may have a curvature. In particular, the angle of inclination of the curvature may increase from 0 degrees to 90 degrees. The inner side 13 extends from the bottom to the end of the fastening adapter. The bottom receives the edge of the window element 12 shown in the drawing as a lower edge. In the operating state, the lower edge can assume any spatial position, depending on the positioning of the optical device 1.

The optical device 1 has a top 20 in the present illustration. The top 20 extends between the front side 4 and the back side 15. A bottom 16 is arranged opposite to the top 20 according to the arrangement of the illustration of FIG. 3. The top 20 needs not necessarily be located upwardly in the operating condition, and the bottom 16 needs not necessarily be located downwardly in the operating condition.

The upper side 20 contains the locking element 3. The locking element 3 includes a lamellar element 22, which may be formed in particular as a resilient blade. According to an embodiment, not shown, the lamellar element 22 between an opening position and a closing position can be displaced. The lamellar element 22 includes a base 23 which is fixed to the optical device 1. In particular, the base 23 may be attached to the housing 24 of the optical device 1. The base 23 opposite the end 25 of the lamellar element 22 may be formed as a hook element or contain a hook element. According to the present exemplary embodiment, the end 25 of the lamellar element 22 projects beyond the front side 4. The hook element has a projection which, in the arrangement according to FIG. 3, surrounds the upper edge of the window element 12.

Figure 4:
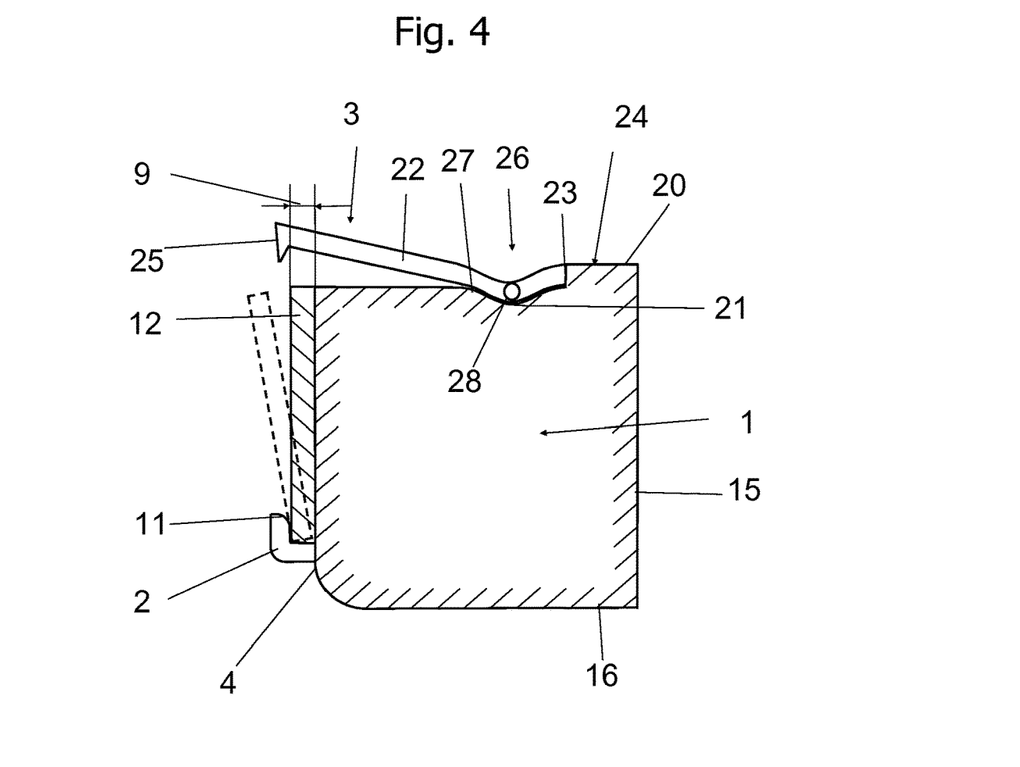
FIG. 4: a detail of the attachment of a window element of the system according to FIG. 3 during assembly or disassembly.

FIG. 4 shows the locking element 3 on the top 20 of the optical device 1 in the opened state. The lamellar element 22 is pushed upwards by the upper edge of the window element 12 to be attached and bounces back into its original position as soon as the window element 12 rests against the front side 4. The hook element of the lamellar element engages around the upper edge of the window element 12 so that the window element 12 is fixed in its position by the fastening adapter 2 and the locking element 3 with respect to the optical device 1, i.e., is temporarily fixed, the lamellar element 22 is pressed at the point 26 against the top 20 of the optical device 1 or its housing 24 to unlock the locking element 3, so that the window element 12 is released. The end 25 is lifted by the contact pressure exerted at the point 26 because the lamellar element 22 performs a rotational movement about an edge 27. The part of the lamellar element 22 between the point 26 and the end 25 thus acts as a lever. The lever arm extending between the end 25 and the edge 27 is longer than the lever arm extending between the edge 27 and the lowest point of the recess 21. A part of the lamellar element 22, which extends from the point 28, which is located above the lowest point of the recess 21, to the base 23, is elastically formed or has a hinge element. In this configuration, the locking element 3 may include a release mechanism for releasing the window element 12. The user can remove the window element 12.

FIG. 5 shows a system 30 comprising a sterile covering 10 comprising a window element 12 and a shell 36, the so-called drape, and an optical device 1 according to FIG. 1. The window element 12 of the sterile covering 10 is connected to the optical device 1, from which only the front side 4 is shown in dotted lines, connected using the locking element 3 and the fastening adapters 2.

In this example, the window element 12 has been inserted into the space between the inner side 13 of the respective fastening adapter 2 for attachment, so that the lower edge of the window element 12 is held by the fastening adapters 2. The upper edge of the window element 12 is moved in the direction of the front side 4. This movement is essentially a rotational movement about an axis of rotation running along the bottom of the fastening adapter 2. As soon as the upper edge of the window element 12 reaches the end 25 of the locking element 3, the locking is released by the contact pressure on the end 25. The end 25 has a leading edge which has an inclination angle with respect to the front side 4. The leading edge of the end 25 is designed such that it is pushed away from the top 20 by a pressure of the upper edge in the present representation. Once the end position of the window element 12 is reached, in which it rests on the front side 4 or a minimum distance from the front side 4, engages with the end 25 of the lamellar element 22 formed as a hook element on the upper edge of the window element 12, whereby a snap mechanism is or will be formed. The window element 12 must be sufficiently rigid, so that it does not buckle, for example, after the latching. For this purpose, the window element 12 according to FIG. 8 can contain at least a first layer and a second layer.

The shell 36 is attached to the window element 12. Materials to be used for the window element 12, can comprise, for example, plastics approved for the sterile environment such as polycarbonate or polyethylene of optical quality. The shell 36 has an opening, wherein this opening is surrounded by an edge region 31 which is delimited by an edge 66. The edge region thereby adjoins the opening of the edge 66. The edge region 31 has a width of 1 to 10 mm, preferably 1 to 5 mm. This opening serves to receive the window element 12. That is, the opening is to be closed by the window element 12.

In particular, the opening has a smaller cross-sectional area than the window element 12. That is, the shell 36 covers the window element 12 in an edge region 31 to the edge 66 when the shell 36 is placed with its opening and the edge region 31 on the window element 12. The edge region 31 of the opening is connected to the sterile side 32 of the window element 12. The sterile side 32 of the window element 12 is the side of the window element 12 facing the sterile outer region 40. The edge region 31 and the window element 12 can be connected using an adhesive bond 65 or welded using heat or ultrasound. If an adhesive bond 65 is provided, the edge region 31 contains splices. If a welded connection is provided, the edge region 31 contains a weld seam. The edge region 31 may be formed in strip form, wherein it is arranged in particular on the window element 12 such that it extends outside the window 5 shown in FIG. 1 or FIG. 2 or at least outside an optically transparent measuring region of the window 5. The edge region 31 can essentially follow the edges of the window element 12 but is at least partially displaced in the region of the fastening adapter 2 and the locking element 3 in the direction of the center of the window 5 or the optically transparent measuring region of the measuring element of the optical device 1. The one or more fastening adapters 2 and the locking element 3 are located outside the edge region 31 when the shell 36 is connected to the window element 12. The surface 34 of the window element 12 enclosed by the edge 66 is thus not covered by the shell 36.

The folding of the shell 36 for use in the sterile surgical environment is known in the art and not the subject of this invention.

Figure 6:
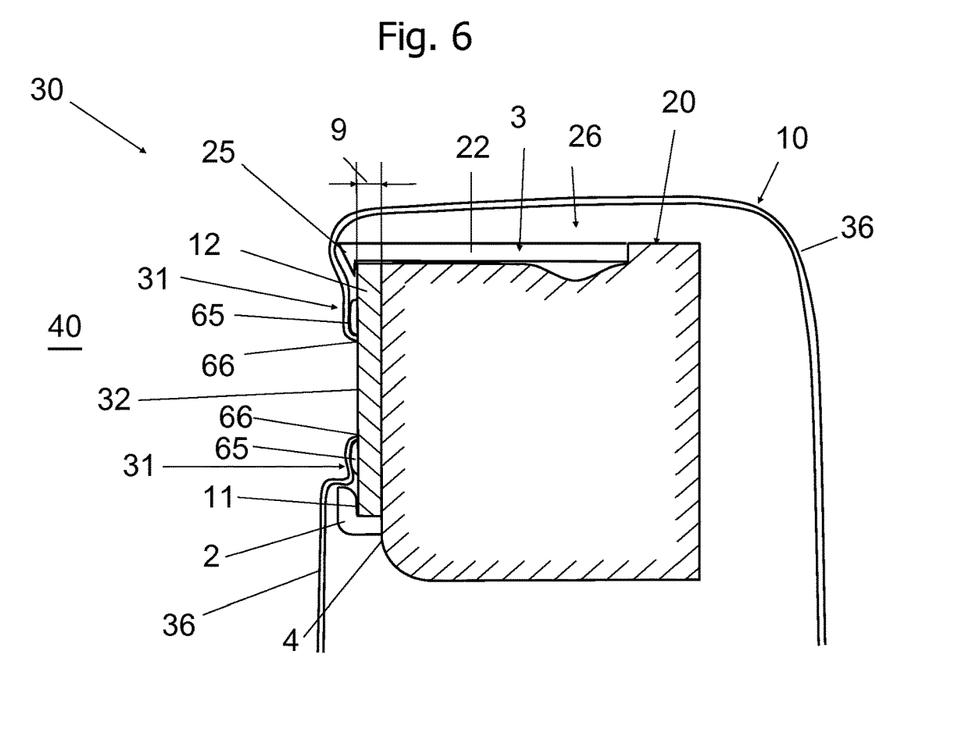
FIG. 6: a section through the system according to FIG. 5, FIG. 7: the back side of the system according to the second embodiment.

FIG. 6 shows a section through a system 30 comprising a sterile covering 10 and an optical device 1 according to the embodiment shown in FIG. 3, FIG. 4 and FIG. 5, respectively. The one or more fastening adapters 2 and the locking element 3 are separated from the sterile outer region 40 together with the optical device 1 by the sterile covering 10. The edge region 31 is arranged on the sterile side 32 of the window element 12. In the edge region 31, the shell 36 is tightly connected to the window element 12. Thereby it is ensured that no substances from the optical device 1 can get into the sterile outer region 40. The window element 12 should not disengage from the attachment even when objects push the optical device 1 by providing, for example, brackets, which also can be attached to the side walls of the window element 12, but which are not visible in FIG. 6.

Figure 7:
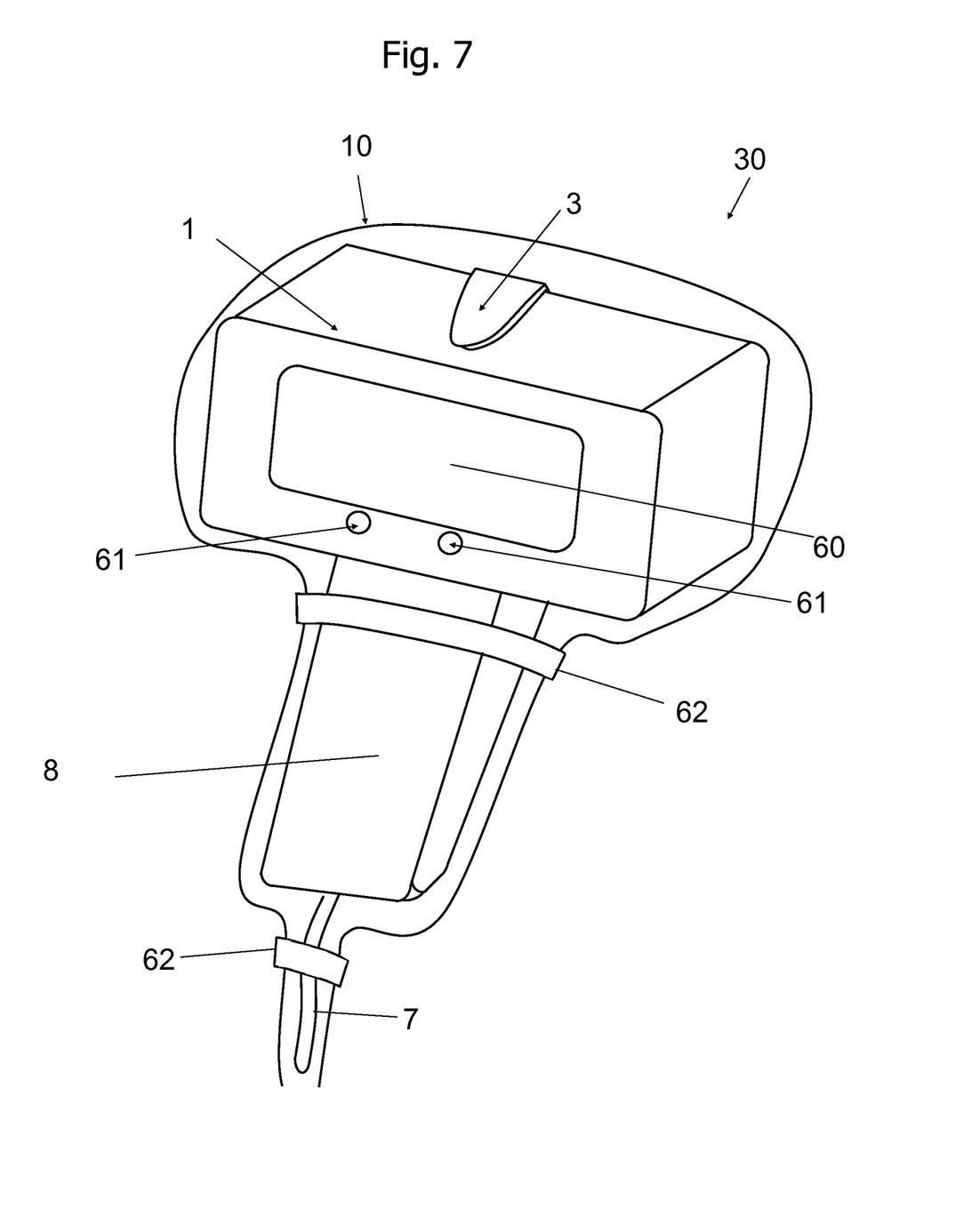

FIG. 7 shows an overview sketch with a sterile covering 10 attached to an optical device 1, with a view of a display element 60 and operating elements 61 of the optical device 1. The sterile covering 10 permits the use of the display and operating elements. A display element 60 may be formed, for example, as a display. An operating element 61 may be formed, for example, as a push button. An operating element can be integrated into the display, which is not shown in the drawing. The sterile covering 10 is held at suitable locations by means of a connecting means 62. The connecting means 62 may contain an element from the group of rubber bands, adhesive tapes, tapes. The optical device can thus be wrapped by means of the one or more connecting means 62 for ergonomic use.

Figure 8:
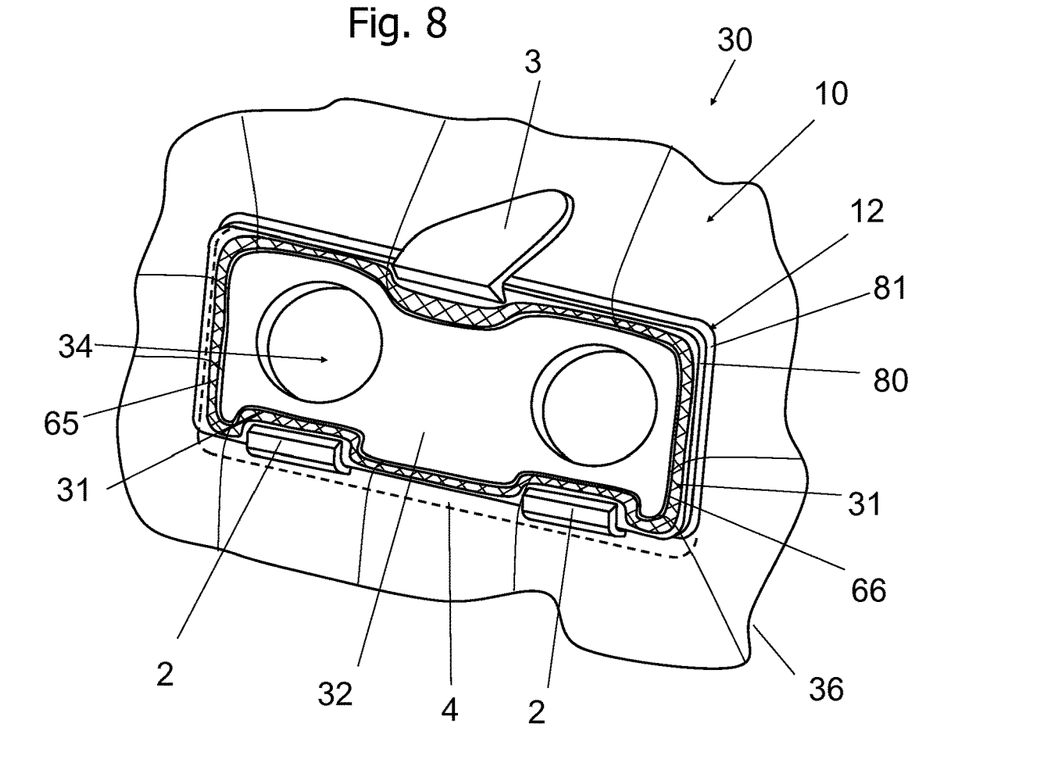
FIG. 8: an overview of a system according to a second variant.

FIG. 8 shows a system 30 comprising a sterile covering 10 comprising a window element 12 and a shell 36 according to a variant for an optical device 1. The same or like parts bear the same reference numerals as in the preceding embodiments and for the description thereof it is referred to previous embodiments. The window element 12 is made up of two layers 80, 81, a first layer 80, which contains the sterile side 32 of the window element 12, and a second layer 81, which adjoins the front side 4.

In particular, either the first layer 80 or the second layer 81 may have at least one opening. Advantageously, the first layer 80 does not include an opening for the sterile side 32 to be formed as a continuous layer so that no leaks can form on the sterile side 32. The first layer 80 is thus formed as a continuous layer. The layer 81 is provided with at least one opening and serves as a mechanical reinforcement or frame for the window element 12. Thus, the required rigidity of the window element 12 is achieved even with a small thickness. The thickness of the window element 12 comprising the first and second layers 80, 81 may, therefore, be less than the thickness of a window element 12 consisting of only a single layer.

The thickness of the window element 12 may be up to 5 mm according to each of the embodiments. The thickness of the window element is preferably at most 3 mm. Particularly preferably, the thickness of the window element is a maximum of 1.5 mm since optical crosstalk for this particularly preferred range can be avoided.

Figure 9:
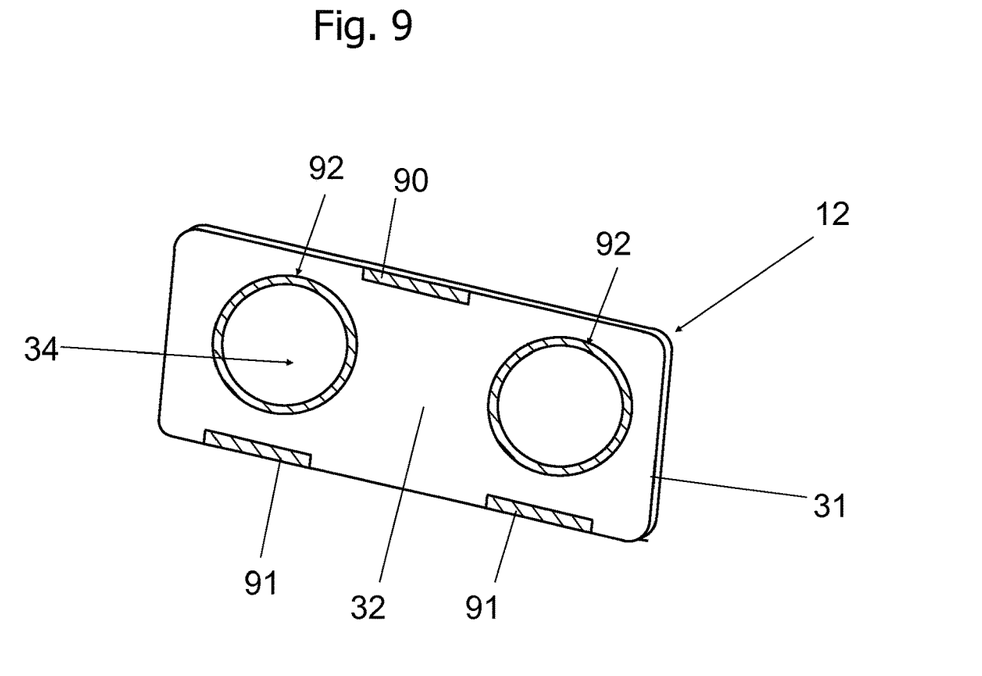
FIG. 9: a printed window element.

FIG. 9 shows an outline sketch of a printed window element 12. The printed areas 90 and 91 are configured as a guide for the correct placement of the window element 12. The two rings 92 in this example reduce the direct optical crosstalk from the active illumination to the imaging system of the optical device 1 in that the color of the rings absorbs the stray light of the active illumination. Both sides of the window element 12 may be printed. At least the imprint of the rings 92 must be suitable for the sterile surgical area.

Figure 10:
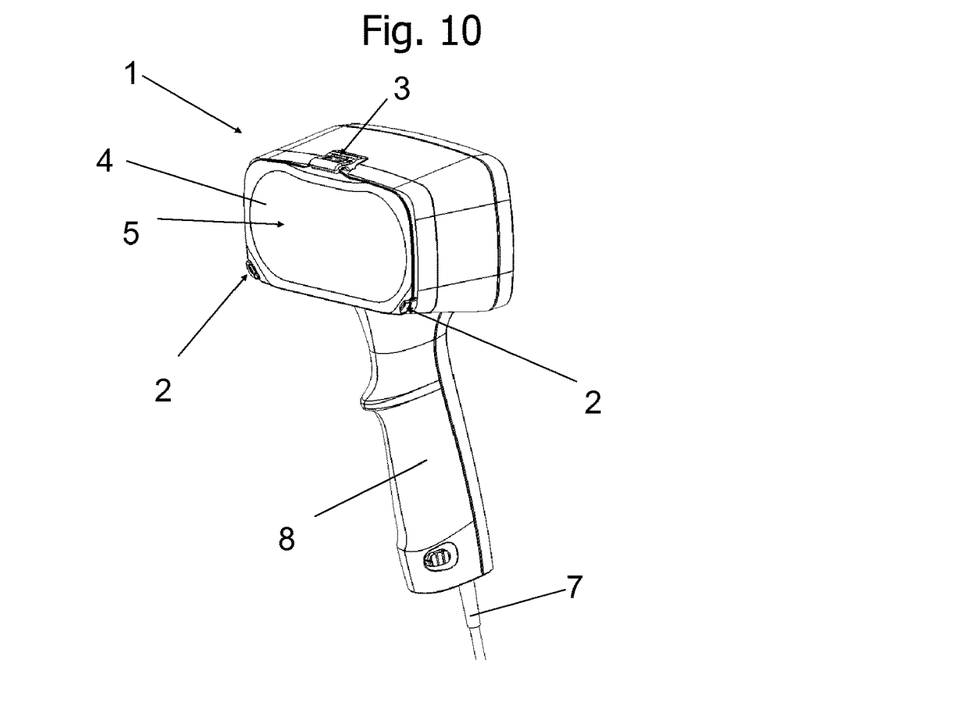
FIG. 10: an optical device according to a third embodiment.

FIG. 10 shows an overview sketch of an optical device 1 using the example of a stereo optical camera system according to a third exemplary embodiment, comprising a fastening adapter 2 and a locking element 3 for a window element 12 of a sterile covering 10, whereby the sterile covering and the window element 12 are omitted in the present representation. The optical side or front side 4 of the optical device 1 according to the present embodiment includes a window 5 associated with the optical device 1, which in the operating state is covered by a window element 12 of the sterile covering 10. According to the present embodiment, two fastening adapters 2 are provided. Instead of two fastening adapters 2, a single fastening adapter can be provided, which is not shown in the drawing. The use of two fastening adapters 2 has the advantage that the window element 12 of the sterile covering 10 is clearly defined in its position. The locking element 3 is used for temporary attachment of the window element 12 of the sterile covering 10 on the optical device 1.

The sketch is completed by a handle 8 and a cable 7 for energy and data transfer to the power supply, evaluation, and display module, not shown here. Alternatively, the cable 7 can be omitted. The power supply can be integrated with the optical device 1. The optical device 1 can communicate with external modules wirelessly. The handle 8 may also be formed as an adapter or include an adapter to connect the optical device 1 fixed to a support or an object, which is not shown in the drawing. The outer surfaces of the optical device 1 are clean, but not sterile.

Figure 11:
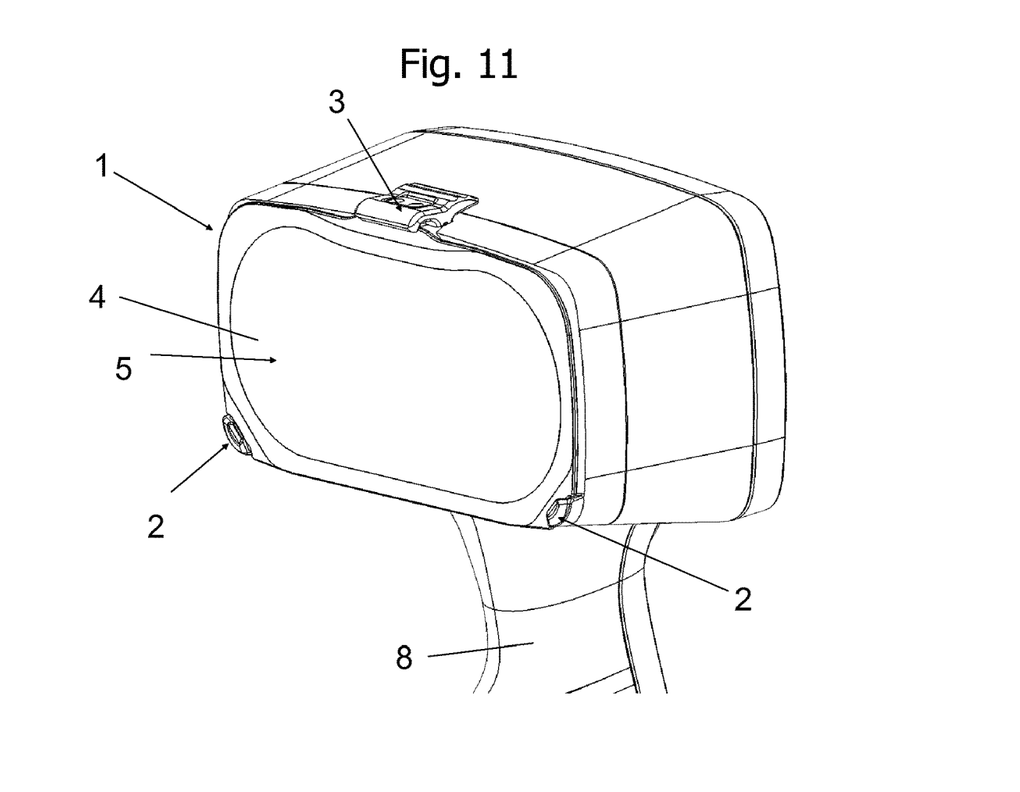
FIG. 11: an enlarged view of the optical device according to FIG. 10, FIG. 12: the front side of the optical device according to FIG. 10 with its window.

FIG. 11 shows the optical device 1 of FIG. 10 in detail. In particular, the fastening adapter 2 and the locking element 3 for the window element 12 are better visible. According to the present embodiment, the fastening of the window element 12 thus takes place at two corner points of the window 5 as well as a side edge of the window 5. The window element 12 is not shown in FIG. 11. The side edge of the window element 12 is held by the locking element 3. The side edge is the upper side edge according to the present illustration. It lies opposite the lower side edge, which forms the connecting line between corner points, which is held by the fastening adapters 2.

Figure 21:
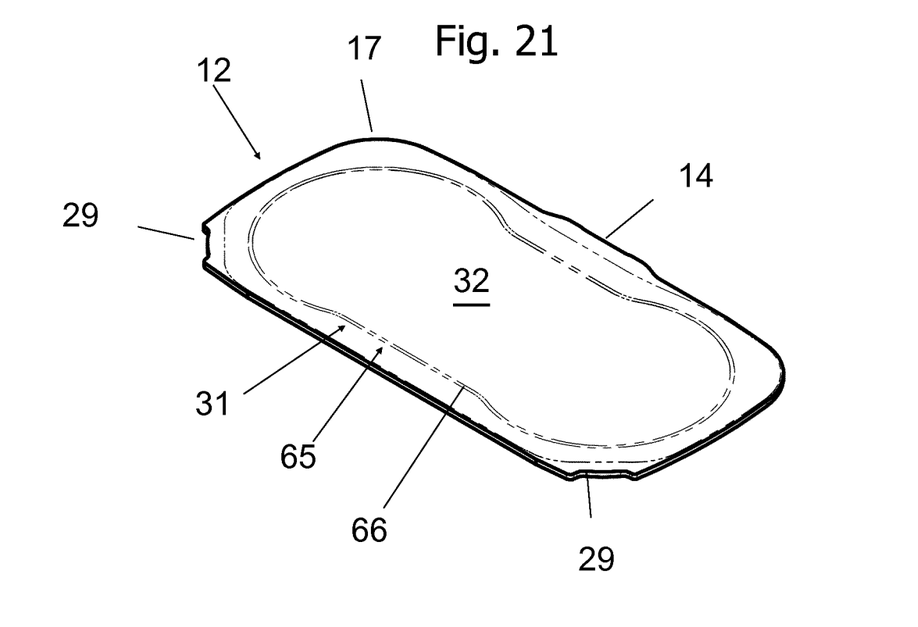

The window element 12 may include a chamfered corner 29, which is visible in FIG. 21. The chamfered corner 29 may be received in the fastening adapters 2 to prevent any displacement in the longitudinal direction of the window element 12 or any displacement in the transverse direction of the window element 12. Therefore, the orientation of the window element 12 is predetermined with respect to the window 5 of the optical device 1, so that in the operating state, the window element 12 can come to lie exactly over the window 5 of the optical device 1.

Figure 12:
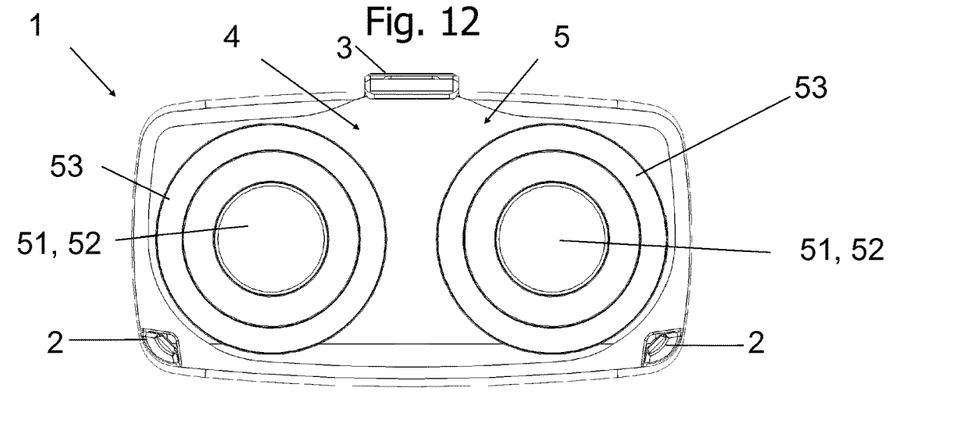

FIG. 12 shows the front side 4 of the optical device with its window 5. The window element 12 is omitted in this illustration. The optical side or front side 4 of the optical device 1 thus according to the present embodiment includes a window 5 associated with the optical device 1. The window 5 may consist of two circular openings for the two imaging systems objective 51 and image sensor 52. The window 5 contains at least one ring 53 for the active illumination of a measurement volume, not shown. The ring 53 may include a light source.

Figure 13:
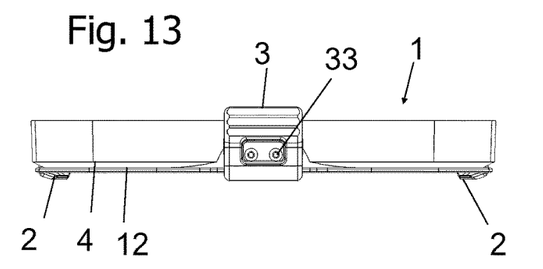
FIG. 13: a detail of the window element and the optical device in a plan view.
Figure 15:
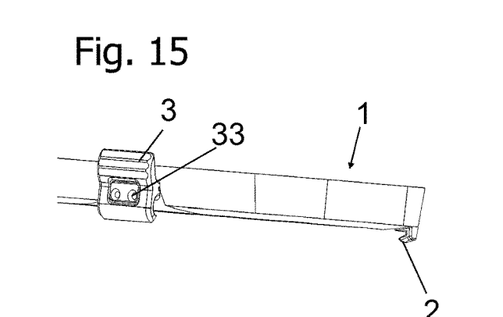
FIG. 15: a detail of the window element and the optical device in a perspective view.

FIGS. 13 and 15 show a detail of the window element 12 and a part of the optical device 1 containing the locking element 3 in a plan view and a perspective view. The locking element 3 fixes the window element 12 on the front side 4 of the optical device 1. The locking element 3 is connected to the optical device by means of a fastening element 33. The fastening element 33 may be formed as a screw, a pin connection or the like, which is attached to a housing element of the optical device 1. The locking element 3 is preferably connected to the optical device in such a way that it is tiltable with respect to the fastening element 33. The locking element 3 according to this embodiment has a substantially rectangular shape in the plan view.

Figure 14:
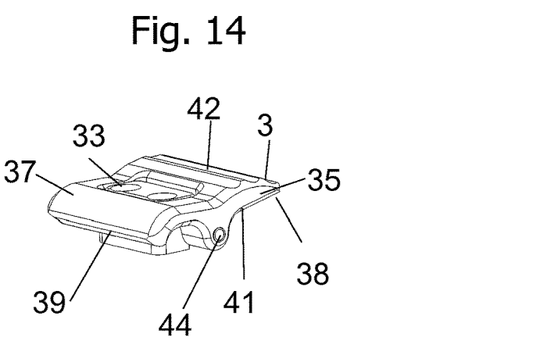
FIG. 14: a detail of a locking element.

FIG. 14 shows the locking element 3 in detail. The locking element 3 has a first side element 35 and a second side element 37. The first side element 35 extends from the fastening element 33 in the direction of the optical device 1. The second side element 37 extends from the fastening element 33 in the direction of the window element 12. The second side element 37 has an edge 39. The surface of the second side element 37 may have a curvature between the fastening element 33 and the edge 39. According to this exemplary embodiment, the curvature is formed in such a way that the edge 39 surrounds the edge of the window element 12, which is visible in FIG. 15, FIG. 17 or FIG. 18.

The first side element 35 has an edge 38. The edge 38 does not rest on the surface of the optical device 1 but is spaced from that surface, which is visible in FIG. 15, FIG. 17 or FIG. 18.

A first side surface 41 extends between the edge 38 and the fastening element 33, which is arranged opposite to the surface of the optical device 1. A second side surface 42 extends between the edge 38 and the fastening element 33, which is directed away from the surface of the optical device 1. At least one of the first or second side surfaces 41, 42 can also include a curvature. The second side surface 42 can include a profiling, such as grooves or ribs. The profiling can serve to improve the grip upon actuation of the locking element 3.

Figure 16:
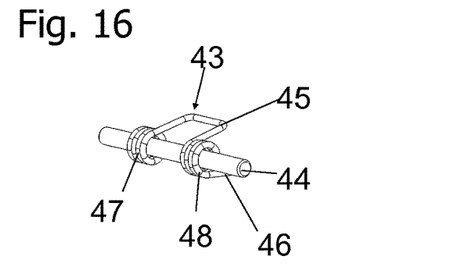
FIG. 16: a detail of a spring element for the locking element according to FIG. 14, FIG. 17: a side view of the optical device, the window element, and the locking element according to FIG. 13, FIG. 18: a detail of FIG. 17, FIG. 19: partial section through an embodiment of a window element.

The locking element 3 can be biased by means of a spring element 43. The spring element 43 is shown in FIG. 16. The spring element 43 comprises a first and a second bracket element 45, 46 and a first and second winding 47, 48, which are arranged on an axis 44. The axis 44 is held in the locking element 3. The first bracket element 45 rests on the first side surface 41 of the first side element 35 of the locking element 3. The second bracket element 45 rests on the surface of the optical device 1. The spring element 43 is biased such that the locking element 3 remains in the locking position, as long as the locking element 3 is not unlocked by manual operation. Thus, the window element 12 surely remains in the protection position in which the window 5 of the optical device 1 is covered by the window element 12.

The spring element 43 holds the locking element 3 according to FIG. 14 closed by means of the second side element 37 and its edge 39, thus, the spring element 43 forms part of an exemplary embodiment of a snap mechanism.

Figure 17:
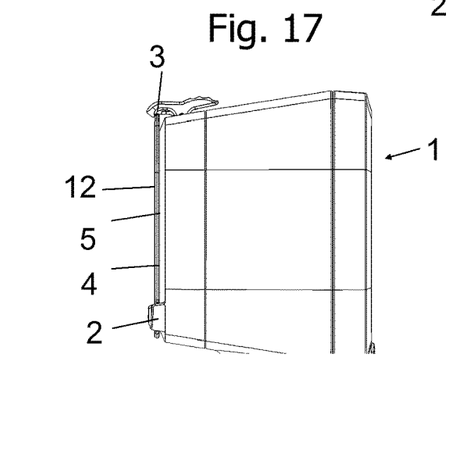

FIG. 17 shows a side view of the optical device, the window element 12 and the locking element 3 and the fastening adapter 2.

In particular, FIG. 17 shows the edge 39 of the second side element 37 of the locking element 3, which surrounds the edge of the window element 12 and fixes the window element 12 with respect to the front side 4 of the optical device 1 such that window 5 is covered by the window element 12. The window element 12 can in particular rest on the window 5, so that no gap remains between the window element 12 and the window 5.

Figure 18:
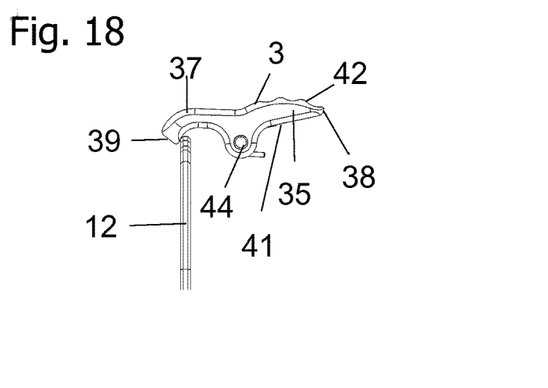

FIG. 18 shows a detail of FIG. 17, in which the optical device 1 is omitted. The locking element 3 is shown in FIG. 18 in section. According to this embodiment, the first side element 35 and the second side element 37 include a cavity. The cavity may be designed to receive a spring element, for example, a spring element 43 according to FIG. 16.

The first side element 35 includes the second side surface 42, which is an embodiment of an unlocking mechanism. The unlocking mechanism is activated by pressure on the second side surface 42. By pressing on the second side surface 42 toward the surface of the optical device 1, the spring element 43 is compressed and the second side element 37 is raised so that the snap mechanism can be released. The pressure may be exerted, for example, by the finger of a user of the system. The spring force of the spring element 43 is preferably set in such a way that the spring force can be overcome by finger pressure.

A locking element 3 according to the embodiment according to one of FIGS. 13 to 18 is easy to operate. If one wishes to remove the window element 12 from the optical device 1, one can exert a pressure on the second side surface 42 of the locking element 3 with a finger. By manual pressure on the second side surface 42, the side surface 42 is rotated about the axis 44, wherein the spring element 43 is compressed by the first side surface 41. The first side element 35 and its edge 39 are thereby moved away from the surface of the optical device 1, raised according to the example shown in FIGS. 13 to 18. The window element 12 can be inserted into the fastening adapter 2 and placed on the window 5. After placement of the window element 12 on the window 5, the locking element 3 can be released, that is, the manual pressure on the locking element 3 removed. The spring element 43 is relaxed, whereby the second side surface 42 and the first side surface 41 moves away from the surface of the optical device 1 and the second side element 37 moves in the direction of the upper side edge of the window element 12. The edge 39 of the second side element 37 projects beyond the window element 12. The second side element 37 has a curvature which partially encloses the upper side edge of the window element 12. The edge 39 of the second side element 37 projects beyond the window element 12. The second side element 37 has a curvature which partially encloses the upper side edge of the window element 12. The curvature may be such that the upper side edge of the window element 12 is moved against the window 5 to rest on the window 5. As a result of the shape of the second side element 37, the window element 12 can thus be brought into abutment with the window 5, so that the window element 12 can be placed immovably on the window 5. The locking element 3 can, in turn, be released by exerting a pressure on the second side surface 42. The second side element then moves away from the upper side edge of the window element 12, whereby the window element 12 can be removed from the window 5.

Alternatively, it is also possible, to release the window element 12 from the locking element 3 by applying a tensile force, which is directed away from the window 5. The upper side edge of the window element 12 exerts pressure on the second side element 37, whereby compression of the spring element 43 and lifting of the second side element 37 can be forced. As a result, the window element 12 can be removed from the window 5 very quickly. The spring force of the spring element 43 is particularly dimensioned such that the window element 12 can be held on one hand without slipping on the window and on the other hand can be removed manually, possibly even without an actuation of the locking element 3. The shape of the edge 39 and the shape of the edge 17 of the window element 12 may be adapted to each other so that they can slide past each other when applying a tensile force. In particular, the edge 39 may have a curvature. The edge 17 may comprise a rounding or a chamfer.

Figure 19:
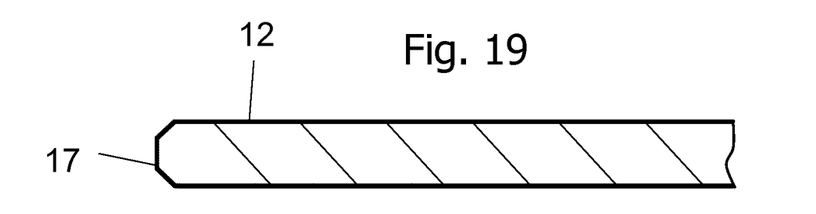

FIG. 19 shows a partial section through an exemplary embodiment of a window element 12. The edge of the window element has chamfers or roundings to reduce the risk of injury when the window element 12 is manipulated. In addition, a shell 36 (see, e.g., FIG. 5) cannot be damaged by an edge of the window element 12 if the shell were to accidentally contact the edge of the window element 12.

Figure 20:
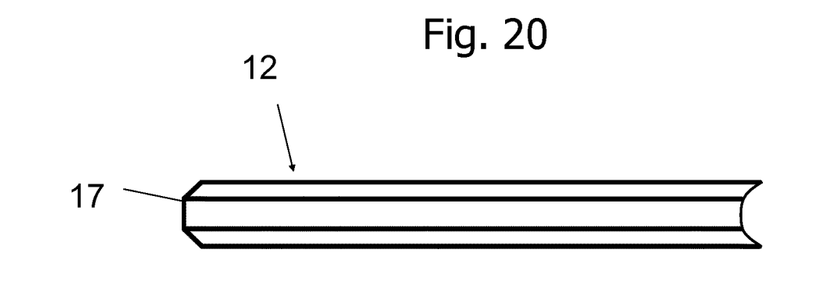
FIG. 20: a side view of the window element according to FIG. 19, FIG. 21: a view of an embodiment of a window element.

FIG. 20 shows a lateral view of a window element 12 according to FIG. 19.

FIG. 21 shows a view of an embodiment of a window element 12. The window element 12 has four edges. Two of these edges limit corners that are not formed as a tip or a rounded tip according to this embodiment, but these edges are obliquely cut to be formed as a beveled corner 29. The shape of the beveled corners 29 is particularly suitable for receiving in a corresponding fastening adapter 2 according to the embodiment shown in FIG. 10, 11. Depending on the number of fastening adapters 2, a corresponding number of beveled corners 29 may be provided. For example, only a single beveled corner 29 may be provided, which is not shown in the drawing. The edge 17, which forms the periphery of the window element 12 and contains the four side edges of the window element 12, may include a chamfer or a rounding. When using an edge 17 which contains a rounded or bevel, the risk of injury or the risk of damage to the system, in particular any damage to the shell 36 or the optical device 1, can be reduced. In addition, a sliding of the edge 17 relative to the edge 39 as described above can be performed, when a tensile force is applied to the window element 12, which is directed away from the window 5.

One of the sides of the window element 12 may include a projection 14. The projection 14 may be intended to be received in a locking element 3 according to one of the preceding embodiments. The projection 14 may be disposed opposite the side edge which extends between the two beveled corners 29. The window element 12 may have an adhesive bond 65. The adhesive bond 65 is located on the sterile side 32 of the window element 12, that is to say on the side of the window element 12 which lies opposite the sterile covering 10.

The adhesive bond 65 may be formed as a double-sided adhesive film. The adhesive bond 65 serves to attach the shell 36 to the sterile side 32 of the window element 12. Instead of an adhesive bond 65, the connection between the window element 12 and the shell 36 may be achieved by ultrasonic welding. The shell 36 is not shown in FIG. 21, it may be formed according to one of the embodiments according to one of FIGS. 5 to 7. The connection, which is here designed as an adhesive bond 65, but according to other embodiments may be formed as a compound produced by ultrasonic welding has a seal against liquids, gases, chemicals, biological or biogenic materials, in particular against pathogens, microbes, viruses, bacteria, prions and the like.

The projection 14 may be arranged axially symmetrically with respect to an axis of symmetry of the window element 12.

The window element 12 according to one of the embodiments may include a coating which contains in particular one element from the group of antistatic, coatings, dirt-repellent coatings, antireflection coatings. In particular, an antireflection coating may be provided to reduce or avoid stray light.

It will be apparent to those skilled in the art that many other modifications are possible in addition to the described embodiments without departing from the inventive concept. The inventive subject matter, therefore, is not to be restricted by the preceding description and encompasses the scope as laid out by the appended claims. Moreover, in interpreting both the specification and the claims, all terms should be interpreted in the broadest possible manner consistent with the context of the claims. In particular, the terms "comprise" and "include" should be interpreted as referring to elements, components, or steps in a non-exclusive manner, indicating that the referenced elements, components, or steps may be present, or utilized, or combined with other elements, components, or steps that are not expressly referenced. Where the specification or the claims refer to at least one of an element or compound selected from the group consisting of A, B, C . . . and N, the text should be interpreted as requiring only one element from the group, not a combination of A plus N, or B plus N, or any other combination of two or more elements or components of this group.

The invention claimed is:

1. A system comprising an optical device and a sterile covering, wherein the sterile covering comprises a window element and a shell, wherein the shell is attached to the window element, wherein the shell has an opening closed by the window element, wherein the shell has an edge region, wherein the edge region is mounted on the window element, wherein the opening is surrounded by the edge region, wherein the opening has a smaller cross-sectional area than the window element, wherein the optical device comprises a locking element for the window element, wherein the shell and the window element are connectable by at least one of an adhesive or a welded connection, and wherein the edge region is arranged at least partially not directly adjacent to edges of the window element.

2. The system according to claim 1, wherein the window element is arranged above a measuring element of the optical device.

3. The system according to claim 1, wherein a fastening adapter is mounted on opposite side edges of the window element.

4. The system according to claim 1, wherein the locking element includes a snap mechanism.

5. The system according to claim 1, wherein the locking element includes an unlocking mechanism.

6. The system according to claim 1, wherein the window element comprises an edge containing a chamfer or a rounding.

7. The system according to claim 1, wherein the shell covers the locking element.

8. The system according to claim 1, wherein the window element is disposed with a sterile side, and wherein the shell is attached to the sterile side.

9. The system according to claim 1, wherein the window element comprises a first layer and a second layer.

10. The system according to claim 9, wherein one of the first or second layers comprises an opening.

11. The system according to claim 9, wherein the first and second layers are joined together by an adhesive bond.

12. The system according to claim 1, wherein the window element is printed on at least one side.

13. The system according to claim 3, wherein the shell covers the fastening adapter.

* * * * *